United States Patent
Seo

(10) Patent No.: US 9,855,120 B2
(45) Date of Patent: Jan. 2, 2018

(54) DENTAL RETENTION SYSTEMS

(71) Applicant: Rodo Medical, Inc., Sunnyvale, CA (US)

(72) Inventor: Young Seo, Sunnyvale, CA (US)

(73) Assignee: Rodo Medical, Inc., San Jose, CA (US)

( * ) Notice: Subject to any disclaimer, the term of this patent is extended or adjusted under 35 U.S.C. 154(b) by 193 days.

(21) Appl. No.: 14/485,430

(22) Filed: Sep. 12, 2014

(65) Prior Publication Data

US 2015/0004564 A1    Jan. 1, 2015

Related U.S. Application Data

(60) Continuation of application No. 14/218,629, filed on Mar. 18, 2014, now Pat. No. 8,845,329, which is a continuation of application No. 13/849,336, filed on Mar. 22, 2013, now Pat. No. 8,678,822, which is a continuation of application No. 13/549,110, filed on Jul. 13, 2012, now Pat. No. 8,403,668, which is a continuation of application No. 13/303,764, filed on
(Continued)

(51) Int. Cl.
*A61C 8/00*      (2006.01)
*A61C 13/235*    (2006.01)

(52) U.S. Cl.
CPC ............ *A61C 8/0075* (2013.01); *A61C 8/005* (2013.01); *A61C 8/0048* (2013.01); *A61C 8/0062* (2013.01); *A61C 8/0065* (2013.01); *A61C 8/0066* (2013.01); *A61C 8/0089* (2013.01); *A61C 13/235* (2013.01); *A61C 2201/007* (2013.01)

(58) Field of Classification Search
CPC ................................................. A61C 2201/007
See application file for complete search history.

(56) References Cited

U.S. PATENT DOCUMENTS 3,328,879 A       7/1967   Bax et al.
3,858,322 A *     1/1975   Padeh ....................... A61C 5/08
                                                           433/204
(Continued)

FOREIGN PATENT DOCUMENTS

JP      2008-212586       9/2008
WO   WO 2008/125852      10/2008
(Continued)

*Primary Examiner* — Jacqueline Woznicki
(74) *Attorney, Agent, or Firm* — Levine Bagade Han LLP

(57) ABSTRACT

Dental retention systems which facilitate the adjustment or removal of an oral appliance, e.g., a crown or bridge, from a reconfigurable abutment assembly are described. The adjustable abutment assembly may be secured to an anchoring implant bored into the bones within the mouth. The abutment assembly has a projecting abutment portion with one or more shape memory alloy compression plates or elements extending along the projecting abutment portion. Each of the plates has a length with one or more straightened portions and with at least one curved or arcuate portion. Energy may be applied to the elements such that the arcuate portion self-flattens to allow for the oral appliance to be placed thereupon while removal of the energy allows the elements to reconfigure into its curved configuration thereby locking the oral appliance to the abutment. Removal of the oral appliance may be effected by reapplication of energy to the elements.

8 Claims, 14 Drawing Sheets

Related U.S. Application Data

Nov. 23, 2011, now Pat. No. 8,221,118, which is a division of application No. 13/021,579, filed on Feb. 4, 2011, now Pat. No. 8,109,764, which is a continuation of application No. 12/504,561, filed on Jul. 16, 2009, now Pat. No. 8,047,844.

(56) References Cited

U.S. PATENT DOCUMENTS

| | | | |
|---|---|---|---|
| 4,144,882 A | | 3/1979 | Takemoto et al. |
| 4,153,060 A | | 5/1979 | Korostoff et al. |
| 4,681,542 A | | 7/1987 | Baum |
| 4,728,330 A | | 3/1988 | Comparetto |
| 5,061,285 A | | 10/1991 | Koch |
| 5,106,299 A | * | 4/1992 | Ghalili ............... A61C 8/0048 433/172 |
| 5,232,364 A | | 8/1993 | Rosen |
| 5,470,230 A | | 11/1995 | Daftary et al. |
| 5,507,826 A | | 4/1996 | Besselink et al. |
| 5,516,288 A | | 5/1996 | Sichler et al. |
| 5,697,779 A | | 12/1997 | Sachdeva et al. |
| 5,791,899 A | * | 8/1998 | Sachdeva ........... A61B 17/0401 433/173 |
| 5,876,434 A | | 3/1999 | Flomenblit et al. |
| 5,951,288 A | | 9/1999 | Sawa |
| 5,979,456 A | | 11/1999 | Magovern |
| 6,710,314 B2 | | 3/2004 | Riess et al. |
| 8,047,844 B2 | | 11/2011 | Seo |
| 8,109,764 B2 | | 2/2012 | Seo |
| 8,221,118 B2 | | 7/2012 | Seo |
| 8,317,515 B2 | | 11/2012 | Seo et al. |
| 8,403,668 B2 | | 3/2013 | Seo |
| 8,491,303 B2 | | 7/2013 | Seo et al. |
| 8,651,864 B2 | | 2/2014 | Seo et al. |
| 2003/0124480 A1 | | 7/2003 | Peacock |
| 2004/0193261 A1 | | 9/2004 | Berreklouw |
| 2006/0154195 A1 | | 7/2006 | Mather et al. |
| 2006/0246396 A1 | | 11/2006 | Suttin et al. |
| 2007/0191879 A1 | | 8/2007 | Gandhi et al. |
| 2008/0090207 A1 | | 4/2008 | Rubbert |
| 2008/0090209 A1 | | 4/2008 | Snaper |
| 2011/0014585 A1 | | 1/2011 | Seo |
| 2011/0123945 A1 | | 5/2011 | Seo |
| 2011/0151397 A1 | | 6/2011 | Seo et al. |
| 2011/0171599 A1 | | 7/2011 | Seo et al. |
| 2012/0064479 A1 | | 3/2012 | Seo |
| 2012/0202173 A1 | | 8/2012 | Seo et al. |
| 2012/0211119 A1 | | 8/2012 | Rule et al. |
| 2013/0011812 A1 | | 1/2013 | Seo |
| 2013/0177873 A1 | | 7/2013 | Seo et al. |
| 2013/0224686 A1 | | 8/2013 | Seo |

FOREIGN PATENT DOCUMENTS

| | | |
|---|---|---|
| WO | WO 2008/147097 | 12/2008 |
| WO | WO 2011/008605 | 1/2011 |
| WO | WO 2012/100672 | 8/2012 |
| WO | WO 2012/106676 | 8/2012 |

* cited by examiner

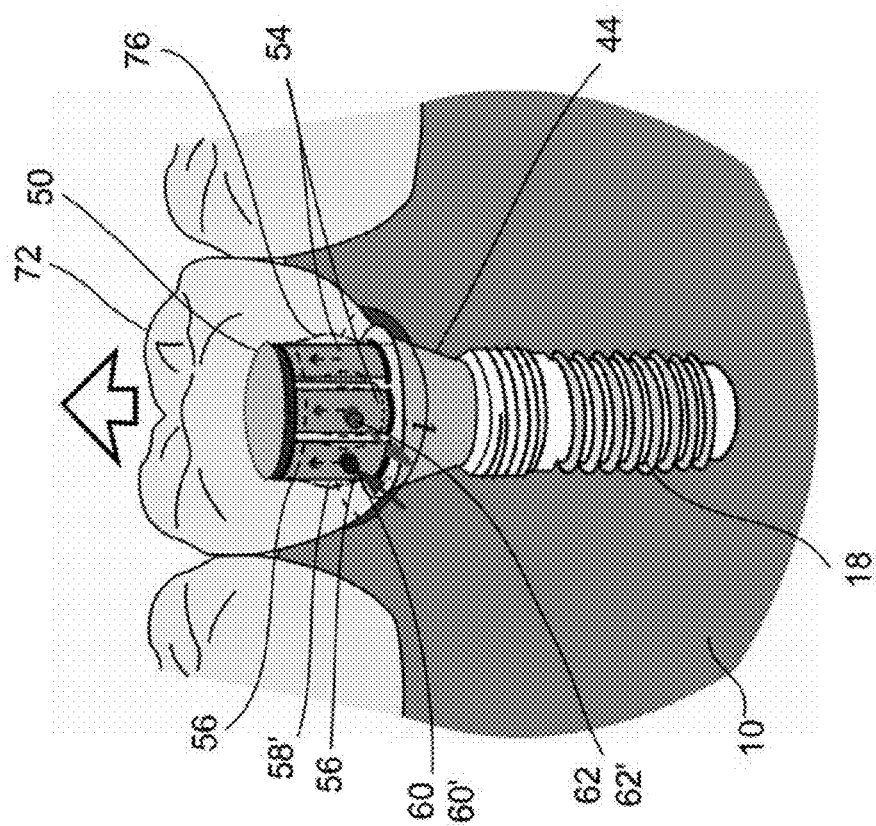
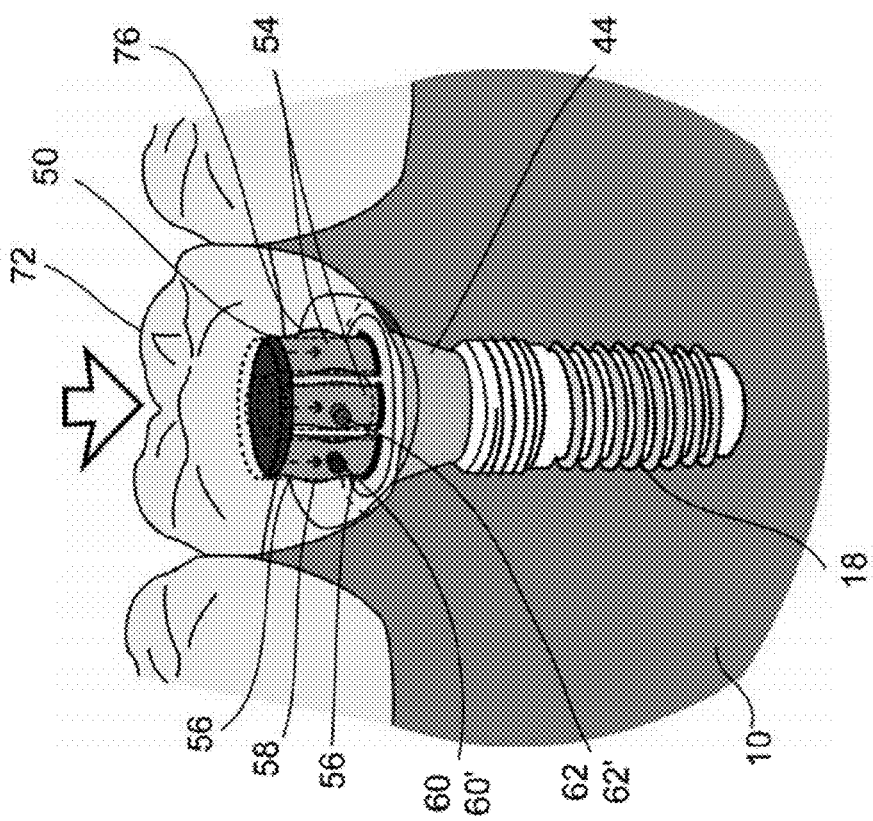

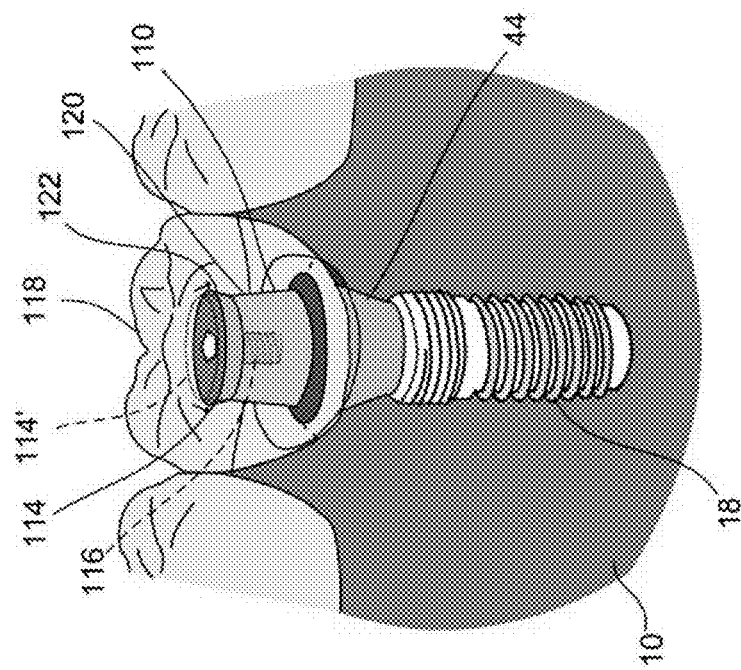
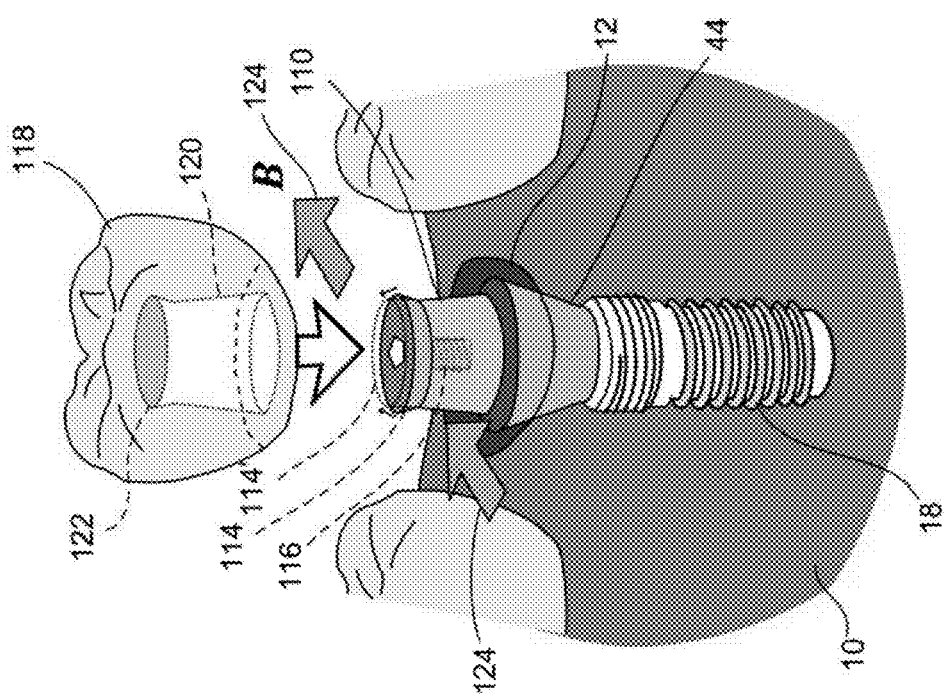
FIG. 6D
FIG. 6C

DENTAL RETENTION SYSTEMS

CROSS-REFERENCE TO RELATED APPLICATIONS

This application is a continuation of U.S. patent application Ser. No. 14/218,629 filed Mar. 18, 2014 (now U.S. Pat. No. 8,845,329), which is a continuation of U.S. patent application Ser. No. 13/849,336 filed Mar. 22, 2013 (now U.S. Pat. No. 8,678,822), which is a continuation of U.S. patent application Ser. No. 13/549,110 filed Jul. 13, 2012 (now U.S. Pat. No. 8,403,668), which is a continuation of U.S. patent application Ser. No. 13/303,764 filed Nov. 23, 2011 (now U.S. Pat. No. 8,221,118), which is a divisional of U.S. patent application Ser. No. 13/021,579 filed Feb. 4, 2011 (now U.S. Pat. No. 8,109,764), which is a continuation of U.S. patent application Ser. No. 12/504,561 filed Jul. 16, 2009 (now U.S. Pat. No. 8,047,844); all of which are incorporated herein by reference in its entirety.

FIELD OF THE INVENTION

The present invention relates to methods and apparatus for retaining one or more dental prostheses in a mouth of a user. More particularly, the present invention relates to methods and apparatus for retaining one or more dental prostheses in a manner which facilitates placement and removal via an actuation mechanism from an anchoring implant and/or abutment.

BACKGROUND OF THE INVENTION

The use of dental prostheses to replace missing or damaged teeth is commonplace. Typically, artificial roots, or implants, are implanted into the bone of the patient's jaw and are used to provide structural support to an intermediate abutment. One or more artificial replacement teeth or crowns are then fastened to the abutment typically by cements or screws.

FIGS. 1A to 1D illustrate partial cross-sectional side views of one example for implanting a typical crown within the mouth of a patient. Depending upon the number of teeth to be replaced, one or more holes may be bored within the bone of the jaw. As shown in FIG. 1A, a portion of the gums or gingiva 14 may be cut open to expose the underlying bone 10, e.g., maxilla or mandible, into which a drill bit 16 may be used to bore open a hole 12. An anchoring dental implant 18, optionally threaded, may be implanted within hole 12 and covered by gingival 14 to allow for healing and for the implant 18 to take hold within bone 10, as shown in FIG. 1B.

Once the implant 18 has been desirably positioned within bone 10, an abutment assembly 20 may be securely attached to implant 18, e.g., by a threaded pin 22 coupling to an implant receiving well 26 defined within implant 18 such that abutment 24, which defines a portion projecting through gingival 14 from implant 18 once coupled to implant 18, as shown in FIG. 1C. With abutment 24 secured to implant 18, crown 28 which defines crown opening 30 may be secured upon abutment 24 by utilizing a number of securement mechanisms, such as cement or a fastener such as a screw. Other securement mechanisms have also included interference fitting, such as with a cross-bar or O-ring type attachment, magnets, etc.

Because the implants, abutments, and crowns are subjected to high compressive and shear forces, initial positioning of the crowns is important not only to provide adequate structural support but also to ensure patient comfort. However, while utilizing cement to attach the crown to the abutment initially allows for aligning the crown more naturally with the dentition of the patient, the tolerance for mistakes is low once the cement has set because of the difficulty and expense in removing a cemented crown from the abutment. Screw-type retention devices may also provide for good securement of the crown to the abutment, but occlusal contact within the patient dentition is often misaligned resulting in a variety of complications. For instance, misaligned crowns result in a compromised occlusal table which in turn may lead to chipping of the crowns as well as poor aesthetic appearance of the patient's dentition.

Previous devices have attempted to create removable denture retention devices, such as that disclosed in U.S. Pat. No. 5,516,288, which is incorporated herein by reference in its entirety. Such systems are described which implant a screw within the jawbone of the patient while utilizing an abutment structure coupled to the implant portion via a ball joint made of shape memory materials. A restorative crown or dental replacement member is then attached to the abutment via conventional retention methods. However, such a device fails to disclose the use of shape memory materials utilized in the interaction between the abutment and the crown or bridge itself, as described in further detail below, as such an interaction facilitates the retention and retrieval of the crown or bridge from the abutment and/or implant.

Accordingly, there exists a need for methods and devices which are efficacious in facilitating not only the retention of oral appliances or prostheses, such as crowns or bridges, along the dentition of a patient but also the removal and/or repositioning of the crown or bridge.

SUMMARY OF THE INVENTION

The assemblies described provide for mechanisms and methods to facilitate the adjustment or removal of an oral appliance or prosthesis, such as a crown or bridge, from a reconfigurable abutment assembly. In utilizing the abutment assemblies described herein, an anchoring implant may be bored into the bones within the mouth of the patient to provide for the structural support of the abutment assembly. Moreover, the implants and abutment assemblies described herein may be utilized in any number of locations within the mouth of the patient, for instance, along the maxilla or mandible or other locations within the body which may benefit from an adjustable abutment assembly as described herein. Additionally, although some of the examples illustrate the placement and/or removal of crowns, various other prostheses for placement within or along the patient dentition may be utilized with the retention devices described herein and are not intended to be limited to use with crowns.

One example of an abutment retaining assembly may have a projecting abutment portion which extends from a first or upper abutment portion to a second or lower abutment portion. A threaded pin may extend from the lower abutment portion for attachment to the implant, which may be bored into the underlying bone to serve as an anchor. Portions of the abutment retaining assembly may be fabricated from any number of biocompatible materials, e.g., gold alloys, stainless steel, nickel-titanium alloys, etc., and may be sized for positioning along the patient's dentition.

With the projecting abutment portion extending from the upper abutment portion, an upper retaining plate may be positioned atop the projecting abutment portion to which one or more compression plates or elements are attached. The compression plates or elements may extend along the projection abutment portion while secured between upper retaining plate and lower retaining portions along the upper abutment portion. The upper retaining plate, as well as the projecting abutment portion, may define an opening for receiving an engagement instrument which may be inserted temporarily within the opening and used to secure the abutment assembly to the anchored implant.

The compression plates or elements may be sized to extend longitudinally along the projecting abutment portion and may number from one element to as many as practicable depending upon their size, e.g., six elements, which are spaced circumferentially about the portion in a uniform manner. Each of the plates has a length with one or more straightened portions with at least one curved or arcuate portion along the length of the element which projects radially when each of the one or more elements are positioned adjacent to one another over portion.

The one or more compression plates or elements may be fabricated from various shape memory alloys, e.g., nickel-titanium alloys such as Nitinol, such that the curved or arcuate portion may be preformed along the element. A phase change may be initiated in the element upon the application of energy, such as heat or electrical energy, to transition the element between its martensitic and austenitic phase such that the arcuate portion may self-flatten with respect to the length of the element. A current or energy, such as an electrical current may be applied to the one or more elements via an input lead contact and return lead contact. If more than a single element is utilized, each of the elements may be electrically coupled to one another to allow for each of the elements to be energized or heated. As the energy is applied to the one or more elements, the phase change may be initiated such that the arcuate portions of elements reconfigure from their curved shape to a straightened shape.

The crown may define a crown opening which is slightly larger in diameter than the abutment assembly in its straightened configuration so that as the crown is lowered upon the abutment assembly, the crown may be tightly fitted thereupon. A portion of the crown opening may further define a widened diameter formed by, e.g., an undercut, which is correspondingly sized to receive the arcuate portions of the elements in their widened diameter. Moreover, the crown may further define corresponding input lead contact and corresponding return lead contact which are positioned along the crown such that the corresponding contacts come into electrical communication with their respective contacts to allow for the transfer of energy directly through the crown and into the elements when the crown is secured to the abutment.

Once the crown has been desirably positioned upon the abutment assembly, the energy may be removed or ceased such that straightened arcuate portions of the elements reconfigure into their arcuate shape. As the arcuate portions reform, the elements may shorten in length thus retracting the upper retaining plate and radially expanding the arcuate portions into the widened diameter of the crown. The reconfigured arcuate portions compress the elements against the widened diameter thereby effectively preventing relative movement between the crown and the elements and locking the crown into position along the abutment.

In the event that the crown requires removal, replacement, or repositioning upon the abutment, energy may again be applied to the elements positioned within the crown through corresponding contacts. As the arcuate portions are reconfigured back into their straightened low-profile configurations, the compression against the interior of the widened diameter may be released and the crown may be adjusted or repositioned upon the abutment or simply pulled entirely off the abutment assembly. A substitute crown may be replaced upon the abutment, if so desired.

A power source may be electrically coupled to a controller, e.g., resistance heating controller, to control the current flow to the one or more elements either directly through the contacts or through the corresponding contacts. As the controller is utilized to control the amount of current, the one or more elements may rise in temperature due to resistance heating. The power source may comprise any number of power supplies, e.g., an AC outlet or batteries, and the power source and controller may be configured into various form factors. The power supplied may range from between, e.g., about 10 to 150 Watts, while the heating time for applying the power may range from, e.g., 0.1 to 2 seconds or longer.

Yet another example for a power source for reconfiguring the one or more elements may utilize inductive heating where the elements may be heated without any direct contact between the power source and the elements. An inductive heating assembly may be regulated with a controller-like variable output oscillator circuit which sends an alternating current through a conductor to one or more coils which then generates an alternating magnetic field between the coils which may be set apart in apposition and at a distance from one another. The distance between the coils may define a receiving channel which is sized to be positioned adjacent to or in proximity to the crown and/or one or more elements.

With the abutment assembly and/or crown positioned within the receiving channel, the alternating magnetic field may be created between the coils to form eddy currents in the one or more elements which causes the material to heat up due to electrical resistance and thus activates the shape memory alloy to initiate their shape change. The frequency of the alternating current and the magnetic field can be set between, e.g., 1 kHz and 1 MHz, depending on the size and configuration of the one or more elements and the targeted activation time. Moreover, the power consumption may range between about, e.g., 10 W to 5 kW.

In yet another variation of a dental retaining assembly, a ferromagnetic shape memory alloy (FSMA) may be configured to have a tapered circumferential edge but when exposed to a magnetic field, the plate may become reconfigured such that the FSMA plate maintains a straightened cylindrical shape from its tapered configuration. As the magnetic field is maintained, the crown defining a crown opening with a widened diameter formed by, e.g., an undercut, may be positioned upon the actuated FSMA plate such that a position of the FSMA plate corresponds to the position of widened diameter. With the crown desirably positioned upon the abutment, the magnetic field may be removed or terminated such that the plate reconfigures into its tapered configuration within the widened diameter and compresses crown into securement upon the abutment.

In yet another alternative, multiple implanted anchoring assemblies may be secured to the patient to allow for the securement of one or more partial bridges utilizing the mechanisms and methods described herein. Accordingly, one or more anchoring assemblies may be used to secure one or more partial bridges. In another example, an overdenture may be secured to the patient utilizing an implanted crossbar configuration which incorporates one or more anchoring assemblies. The anchoring assemblies may similarly utilize the one or more elements to secure the overdenture within the patient mouth.

BRIEF DESCRIPTION OF THE DRAWINGS

FIG. 2C illustrates a perspective view where the shape memory elements may be reconfigured into their expanded configuration to secure the crown upon the abutment.

FIG. 2D illustrates a perspective view showing how energy may be reapplied to the elements through the crown to yet again configure the elements into a low-profile shape to allow for the repositioning or removal of the crown from the abutment.

FIG. 6C illustrates a magnetic field applied to the FSMA plate to configure its shape into a low-profile to receive a crown.

FIG. 6D illustrates the positioning of the crown upon the FSMA plate and the reconfiguration of the FSMA plate into its expanded profile to secure the crown thereto.

DETAILED DESCRIPTION OF THE INVENTION

In positioning and securing an oral appliance, such as a crown or bridge, within the mouth of a patient, the retaining assemblies described herein allow not only for secure attachment but also for adjustment of the crown or bridge along the patient's dentition. The assemblies described also provide for mechanisms and methods to facilitate the entire removal of the crown or bridge from the abutment. In utilizing the abutment assemblies described herein, any number of typical anchoring implants may be bored into the bones within the mouth of the patient to provide for the structural support of the abutment assembly. Moreover, the implants and abutment assemblies described herein may be utilized in any number of locations within the mouth of the patient, for instance, along the maxilla or mandible or other locations within the body which may benefit from an adjustable abutment assembly as described herein.

Figures 1A, 1B, 1C, 1D:
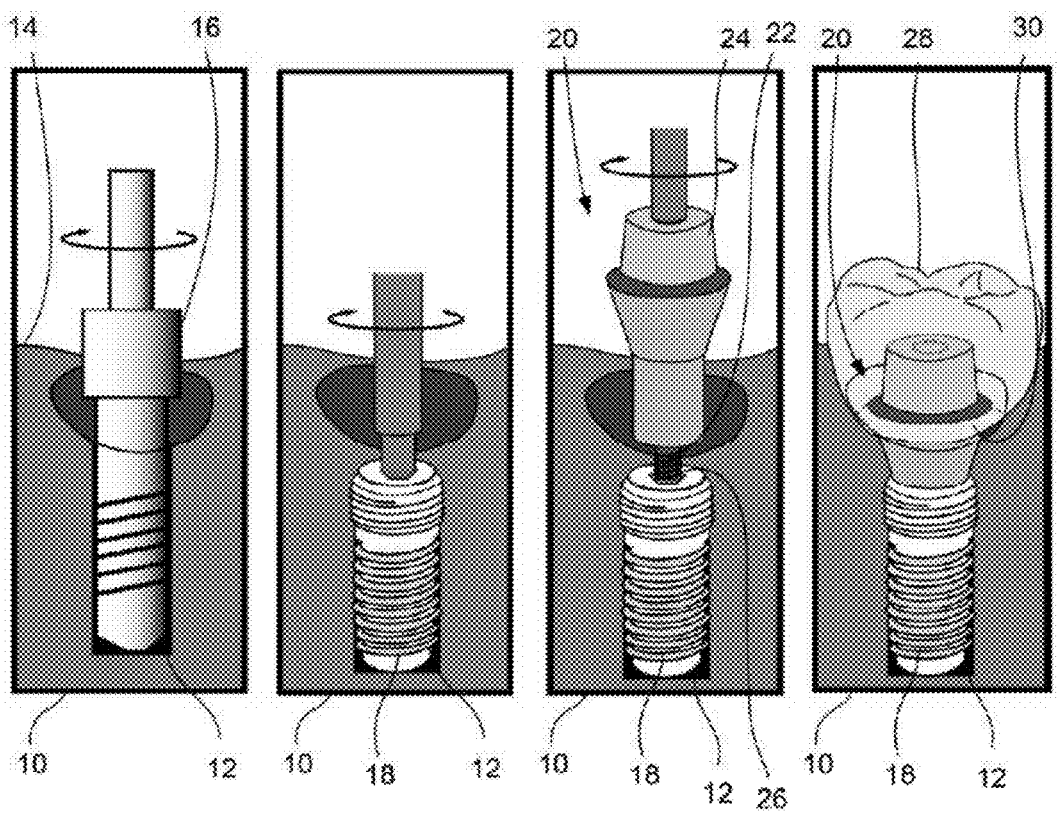
FIGS. 1A to 1D illustrate partial cross-sectional profiles of an example of placing an implant within a jawbone of a patient and attaching a crown thereto.
Figure 2A:
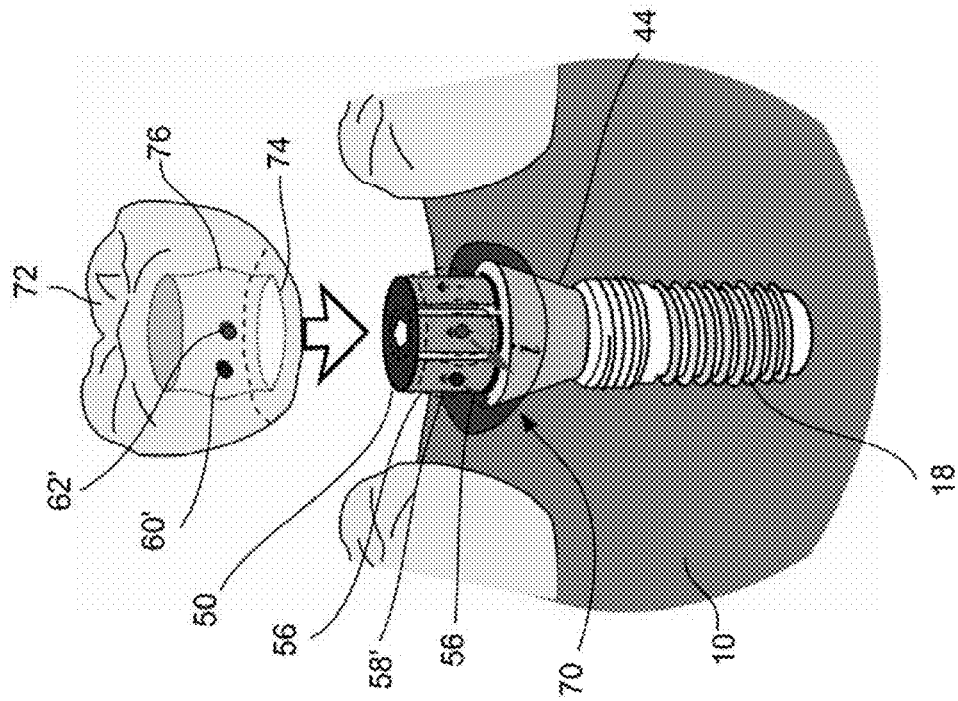
FIG. 2A illustrates a perspective view of attaching one variation of an abutment retaining assembly to a conventional implant.

Turning now to FIG. 2A, one example of an abutment retaining assembly 40 is illustrated as having a projecting abutment portion 42 which extends from a first or upper abutment portion 44, which is optionally tapered, to a second or lower abutment portion 46. A threaded pin 48 may extend from the lower abutment portion 46 for attachment to implant 18, which may be bored into the underlying bone 10 to serve as an anchor, and as previously described, which may be adjacent to another crown or pre-existing tooth or teeth 68. Portions of the abutment retaining assembly 40 may be fabricated from any number of biocompatible materials, e.g., gold alloys, stainless steel, nickel-titanium alloys, etc., and may be sized for positioning along the patient's dentition. For instance, the assembly 40 may have a diameter ranging from, e.g., 2 to 6 mm, with a length ranging from, e.g., 5 to 15 mm. These dimensions are exemplary and are not intended to be limiting.

Figure 6A:
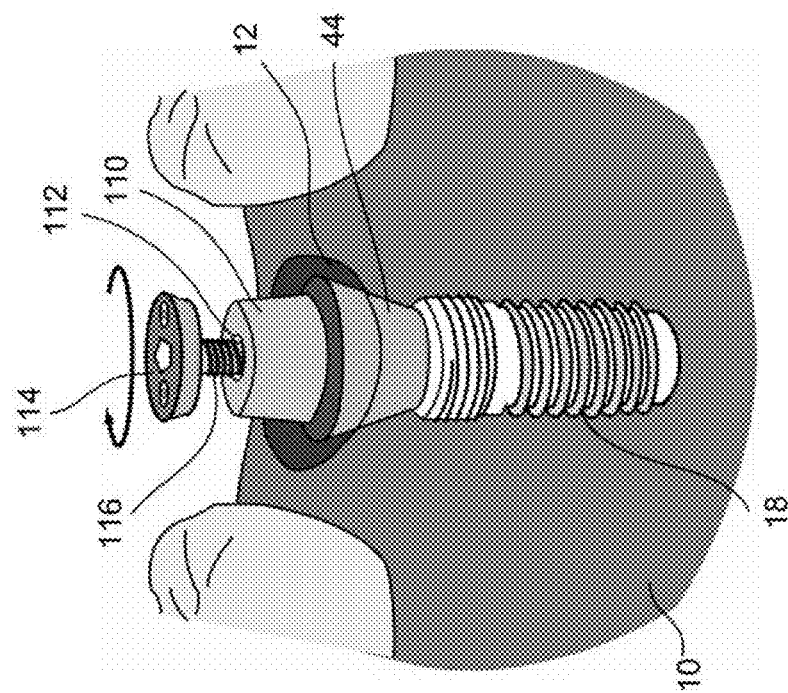
FIG. 6A illustrates an example of another variation for securing a crown where an abutment retaining assembly is secured to an implant.

With the projecting abutment portion 42 extending from the upper abutment portion 44, an upper retaining plate 50 may be positioned atop the projecting abutment portion 42 to which one or more compression plates or elements 54 are attached. The compression plates or elements 54 may extend along the projection abutment portion 42 while secured between upper retaining plate 50 and lower retaining portions 52 along the upper abutment portion 44. The upper retaining plate 50, as well as projecting abutment portion 42, may define an opening 64, which may be optionally keyed, for receiving an engagement instrument 66 (as shown in FIG. 6A) which may be inserted temporarily within opening 64 and used to secure abutment assembly 40 to the anchored implant 18, e.g., by rotating abutment assembly 40 so as to screw threaded pin 48 into implant 18.

The compression plates or elements 54 may be sized to extend longitudinally along projecting abutment portion 42 and may number from one element to as many as practicable depending upon their size, e.g., six elements, which are spaced circumferentially about portion 42 in a uniform manner. Each of the plates are illustrated as having a length with one or more straightened portions 56 with at least one curved or arcuate portion 58 along the length of the element 54 which projects radially when each of the one or more elements 54 are positioned adjacent to one another over portion 42, as illustrated.

In one example, each of the elements 54 may range in length from, e.g., about 5 to 10 mm, with a thickness of, e.g., about 0.5 to 1.5 mm. Moreover, the curved or arcuate portion 58 may have a radius which defines a height of, e.g., about 1 to 2 mm, relative to the thickness of the element 54 such that when element 54 is reconfigured into a straightened configuration, element 54 may extend an additional, e.g., 1.5 to 3 mm in length. These dimensions are provided as exemplary values and are not intended to be limiting. Variations in dimensions may be utilized as practicable.

Figure 2B:
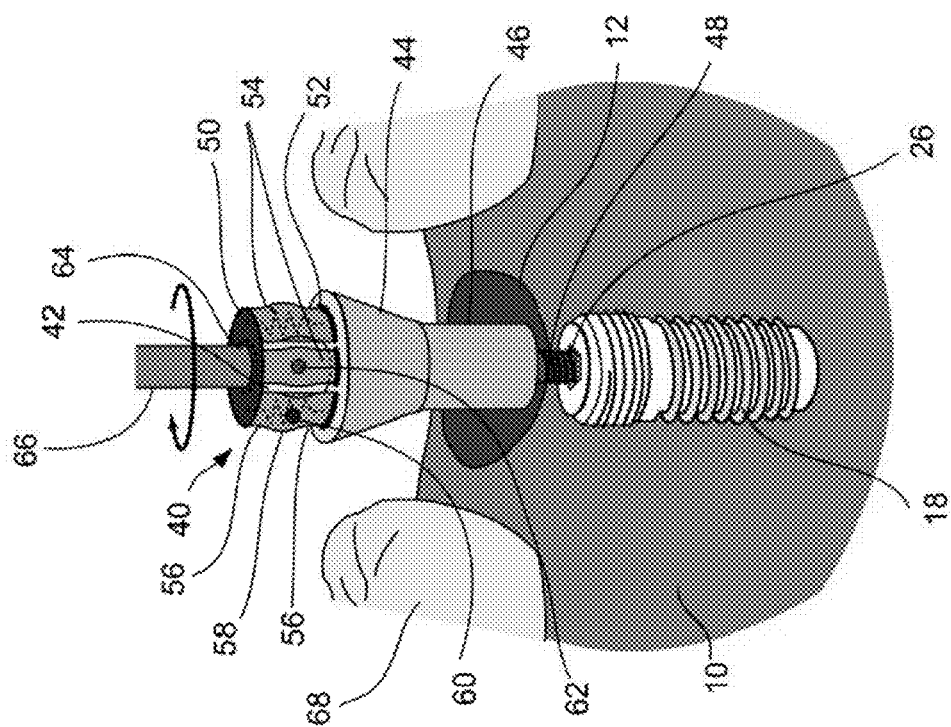
FIG. 2B illustrates a perspective view where energy may be applied to one or more shape memory compression plates or elements positioned along the abutment retaining assembly to configure the elements into a low-profile shape such that a crown may be received upon the abutment.

The one or more compression plates or elements 54 may be fabricated from various shape memory alloys, e.g., Nitinol, such that the curved or arcuate portion 58 may be preformed along the element 54. A phase change may be initiated in the element 54 upon the application of energy, such as heat or electrical energy, to transition the element 54 between its martensitic and austenitic phase such that the arcuate portion 58 may self-flatten with respect to the length of the element 54. As illustrated in FIG. 2B, current or energy 70, such as an electrical current i, may be applied to the one or more elements 54 via an input lead contact 60 and return lead contact 62. If more than a single element 54 is utilized, each of the elements 54 may be electrically coupled to one another to allow for each of the elements 54 to be energized or heated. The lead contacts 60, 62 may be positioned along a single element or different elements so long the elements are in electrical communication. As the energy is applied to the one or more elements 54, the phase change may be initiated such that the arcuate portions 58 of elements 54 reconfigure from their curved shape to a straightened shape, as shown in the figure.

With the arcuate portions 58 reconfigured into straightened portions 58', upper retaining plate 50 may be moved longitudinally with respect to upper abutment portion 44 while the elements 54 remain attached to their lower retaining portions 52. The resulting outer diameter of the elements 54 upon the abutment may be reduced from, e.g., about 6 mm to about 4 mm, to thus allow for the placement of a crown 72 upon the abutment assembly. Crown 72 may define a crown opening 74 which is slightly larger in diameter than the abutment assembly in its straightened configuration so that as crown 72 is lowered upon the abutment assembly, crown 72 may be tightly fitted thereupon. A portion of crown opening 74 may further define a widened diameter 76 formed by, e.g., an undercut, which is correspondingly sized to receive the arcuate portions 58 of elements 54 in their widened diameter, as described below. Moreover, crown 72 may further define corresponding input lead contact 60' and corresponding return lead contact 62' which are positioned along crown 72 such that the corresponding contacts 60', 62' come into electrical communication with their respective contacts 60, 62 to allow for the transfer of energy directly through the crown and into the elements 54 when the crown is secured to the abutment. To guide the crown 72 upon the abutment assembly, the opening 74 of crown 72 may be optionally keyed or shaped in a predetermined manner which corresponds with a configuration of the abutment such that advancement of the crown 72 upon the abutment may be achieved in a specified orientation, if so desired.

Once crown 72 has been desirably positioned upon the abutment assembly, the energy may be removed or ceased such that straightened arcuate portions 58' of elements 54 reconfigure into their arcuate shape. As the arcuate portions 58 reform, the elements 54 may shorten in length thus retracting upper retaining plate 50 and radially expanding the arcuate portions 58 into the widened diameter 76 of crown 72, as shown in FIG. 2C. The reconfigured arcuate portions 58 compress the elements 54 against the widened diameter 76 thereby effectively preventing relative movement between the crown 72 and the elements 54 and locking the crown 72 into position along the abutment. The compressive force which may be generated between the elements 54 and the crown interior may range, e.g., between 10 N to 10 kN, to effectively lock the crown 72 into position.

In the event that crown 72 requires removal, replacement, or repositioning upon the abutment, energy may again be applied to the elements 54 positioned within the crown 72 through corresponding contacts 60', 62' which are in electrical communication with their respective contacts 60, 62, as shown in FIG. 2D. As the arcuate portions 58 are reconfigured back into their straightened low-profile configurations 58', the compression against the interior of widened diameter 76 may be released and crown 72 may be adjusted or repositioned upon the abutment or simply pulled entirely off the abutment assembly. A substitute crown may be replaced upon the abutment, if so desired.

Figure 3:
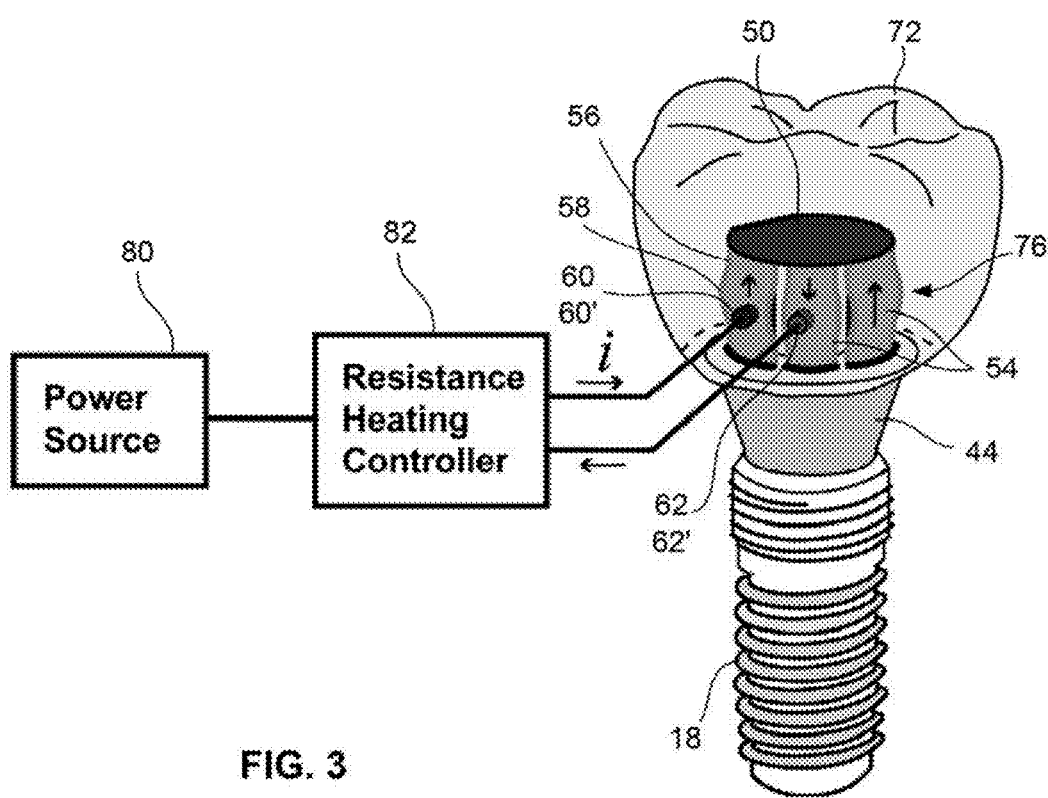
FIG. 3 illustrates an example of how energy may be applied via a power source and controller to the one or more elements.

In delivering the energy to the one or more elements 54 for initiating the phase change in the shape memory alloy, FIG. 3 illustrates one example which delivers a current to elements 54. A power source 80 may be electrically coupled to a controller 82, e.g., resistance heating controller, to control the current flow to the one or more elements 54 either directly through contacts 60, 62 or through corresponding contacts 60', 62' if delivered through crown 72. In either case, as the controller 82 is utilized to control the amount of current, the one or more elements 54 may rise in temperature due to resistance heating. The power source 80 may comprise any number of power supplies, e.g., an AC outlet or batteries, and the power source 80 and controller 82 may be configured into various form factors. For example, the heating assembly may be configured into a hand-held unit which is portable by the user or it may be configured into a larger non-portable unit. Because the size, configuration, and thermal conductivity of the elements 54 may be varied, the amount of power applied and the heating time may be varied accordingly. For instance, the power supplied may range from between, e.g., about 10 to 150 Watts, while the heating time for applying the power may range from, e.g., 0.1 to 2 seconds or longer.

Figure 4:
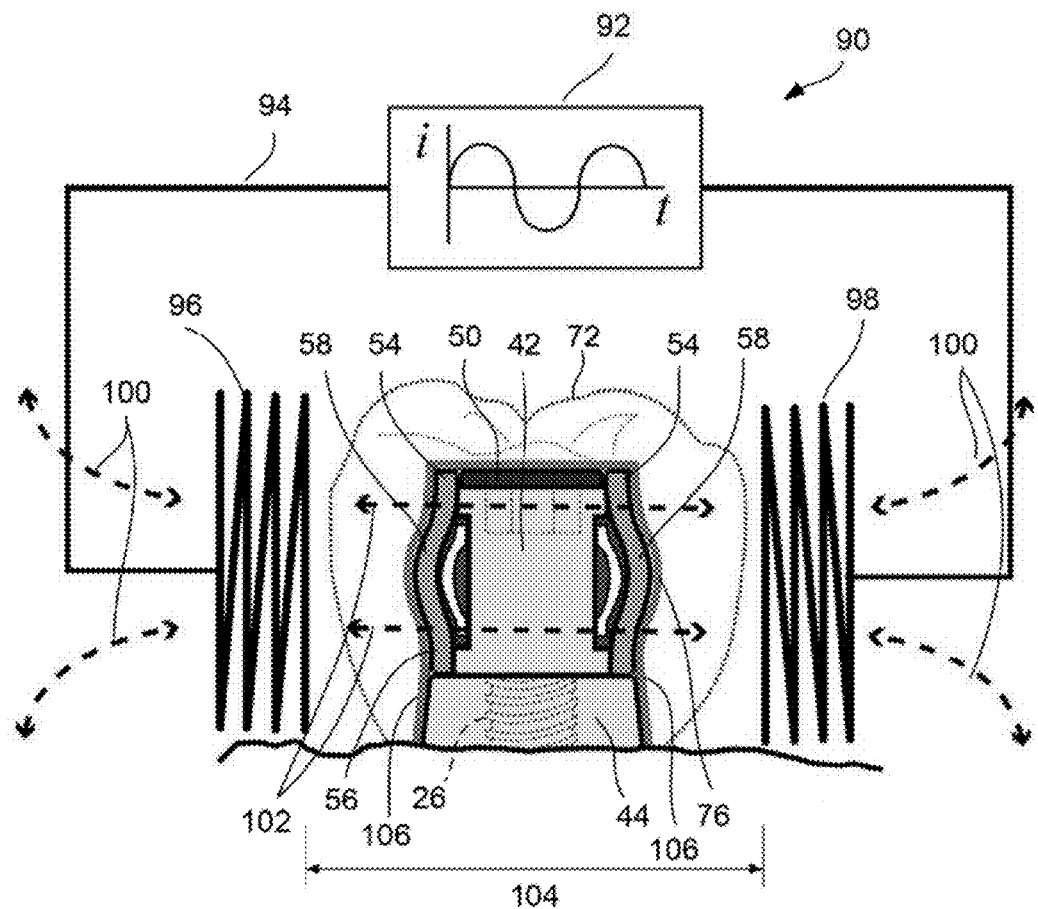
FIG. 4 illustrates schematically another example of how an alternating magnetic field may be applied to the one or more elements by inductively transferring energy to reconfigure the shape of the elements.

Yet another example for a power source for reconfiguring the one or more elements 54 is illustrated schematically in FIG. 4. Because this particular variation may utilize inductive heating, the elements 54 may be heated without any direct contact between the power source and the elements 54. As shown, an inductive heating assembly 90 may be regulated with a controller-like variable output oscillator circuit 92 which sends an alternating current i through conductor 94 to one or more coils 96, 98 which then generates an alternating magnetic field 100 between the coils 96, 98, which may be set apart in apposition and at a distance from one another. The distance between the coils 96, 98 may define a receiving channel 104 which is sized to be positioned adjacent to or in proximity to the crown 72 and/or one or more elements 54 such that when the elements 54 are to be reconfigured, the heating assembly 90 may be positioned upon the abutment assembly and/or crown 72 within the user's mouth.

With the abutment assembly and/or crown 72 positioned within receiving channel 104, the alternating magnetic field 100 may be created between coils 96, 98 to form eddy currents 102 in the one or more elements 54. These eddy currents 102, which may also be described as the movement of electrons in the material, causes the material to heat up due to electrical resistance and thus activates the shape memory alloy to initiate their shape change. The frequency of the alternating current i and the magnetic field can be set between, e.g., 1 kHz and 1 MHz, depending on the size and configuration of the one or more elements 54 and the targeted activation time. Moreover, the power consumption may range between about, e.g., 10 W to 5 kW. As described above, the heating assembly 90 may be configured, e.g., as a portable hand-held unit or as a larger non-portable unit. Additional details and examples of an inductive heating assembly are further shown in U.S. Pat. No. 6,710,314, which is incorporated herein by reference in its entirety.

Additionally in this and other examples, a sealant 106, such as a biodegradable silicone material, may be placed within the crown cavity to at least partially encompass or encase the abutment assembly to create a water-tight seal. This sealant 106 may completely encase the abutment assembly or it may seal just around a portion of the assembly, such as upper abutment portion 44.

Figure 5:
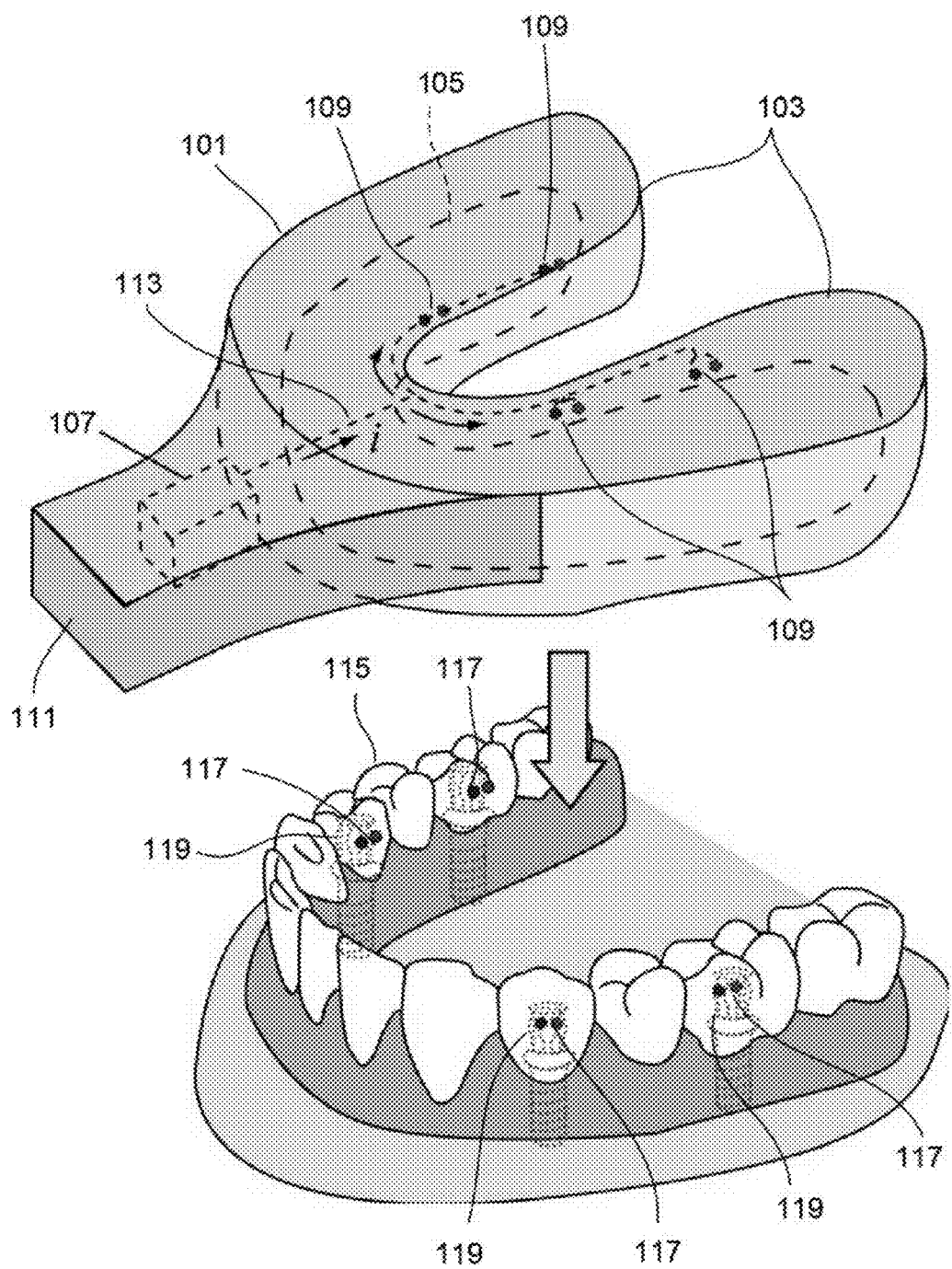
FIG. 5 illustrates a housing configured into a mouthpiece for applying energy to the compression elements.

In applying the energy (either resistive or inductive heating) to the one or more compression elements, one variation of a housing 101 configured into the form of a mouthpiece which may be inserted temporarily into the mouth of a patient is shown in the perspective assembly view of FIG. 5. Housing 101 may generally comprise two biteplates 103 which extend from a handle 111 and which define a receiving cavity 105 for receiving within or placement against a dental prosthesis such as an overdenture, crown, etc. Other variations may comprise a single biteplate or a partial biteplate depending upon the dental prosthesis to be secured. Moreover, handle 111, which generally extends from the mouth of the patient, may be removed or omitted entirely.

In either variation, one or more contacts 109 may be defined along the receiving cavity 105 and are in electrical communication with a power supply 107 through electrical conductor 113, which may be routed through the housing 101 to each of the respective contacts 109. In use, with one or more anchoring assemblies 119 secured within the patient's mouth, the dental prosthesis 115 (or prostheses) may either be positioned directly upon the respective anchoring assembly 119 or the dental prosthesis 115 may be positioned within receiving cavity 105 of housing 101. The housing 101 may then be positioned within the patient's mouth such that the respective dental prosthesis 115 is either placed upon a corresponding anchoring assembly 119 and/or such that the one or more contacts 109 positioned within housing 101 is aligned with a corresponding contact 117 positioned along the dental prosthesis. In either case, once the respective contacts 109, 117 are aligned, power supply 107 may be activated to actuate the compression plates to reconfigure and secure the dental prosthesis 115 to the one or more anchoring assemblies 119. Once the dental prosthesis 115 is fully secured, housing 101 may be removed from the patient's mouth. Housing 101 may be reinserted into the patient's mouth to reverse the securement process for readjusting or entirely removing the prostheses from the anchoring assemblies 119, if so desired. Moreover, housing 101 may be optionally used by the patient for inserting and/or removing prostheses such as overdentures on a daily basis or it may also be used by a practitioner for securing and/or removing any number of dental prostheses.

Figure 6B:
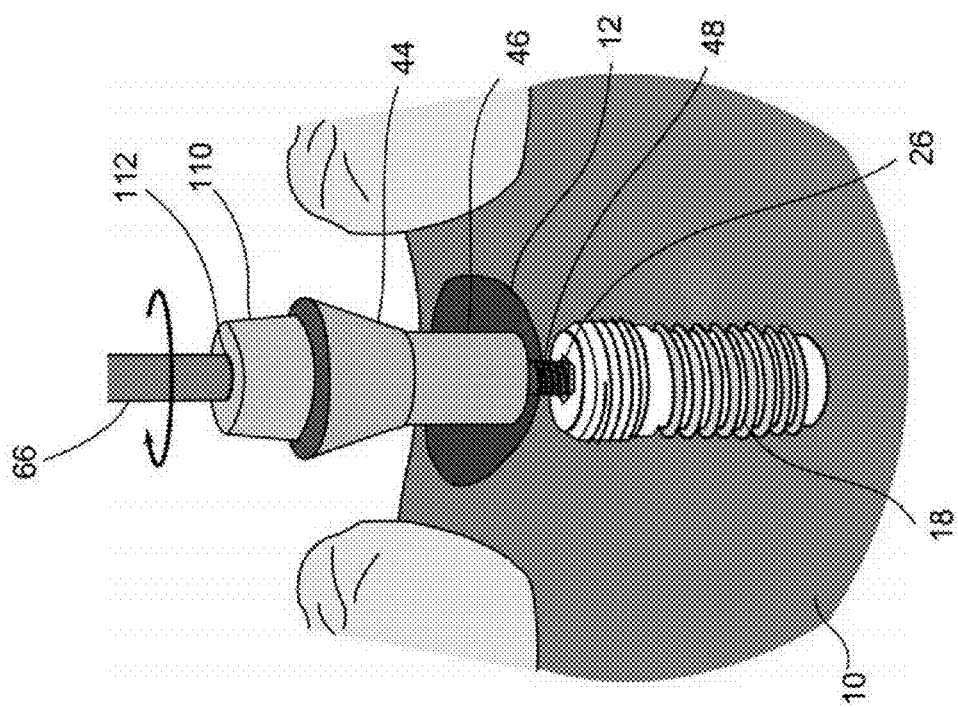
FIG. 6B illustrates a reconfigurable ferromagnetic shape memory alloy (FSMA) plate which may be secured to the abutment.

In yet another variation of a dental retaining assembly, FIG. 6A illustrates an example of an assembly which may utilize a ferromagnetic shape memory alloy (FSMA), which are ferromagnetic materials which generally exhibit relatively large changes in shape and size when exposed to a magnetic field. In this variation, an abutment assembly having a projecting abutment portion 110 extending from an upper abutment portion 44 may be connected to an implant 18 via a threaded pin 26, as previously described. With the abutment secured to implant 18, a circular FSMA plate 114 having a tapered circumferential edge may be attached to the abutment opening 112 via a threaded retaining pin 116, which may be optionally keyed with respect to opening 112, as shown in FIG. 6B. Although illustrated as a circular element, FSMA plate 114 may be configured into various shapes or sizes depending upon the coupling mechanism to the crown.

The FSMA plate 114 may be configured to have a tapered circumferential edge but when exposed to a magnetic field 124, as shown in FIG. 6C, the plate 114 may become reconfigured such that the FSMA plate 114' maintains a straightened cylindrical shape from its tapered configuration. As the magnetic field 124 is maintained, crown 118 defining a crown opening 120 with a widened diameter 122 formed by, e.g., an undercut, may be positioned upon the actuated FSMA plate 114' such that a position of FSMA plate 114' corresponds to the position of widened diameter 122. With the crown 118 desirably positioned upon the abutment, the magnetic field 124 may be removed or terminated such that the plate 114 reconfigures into its tapered configuration within the widened diameter 122 and compresses crown 118 into securement upon the abutment, as shown in FIG. 6D. Also as described above, crown 118 may be configured to keyed to be positioned upon the abutment in a predetermined orientation, if so desired.

Figure 7A:
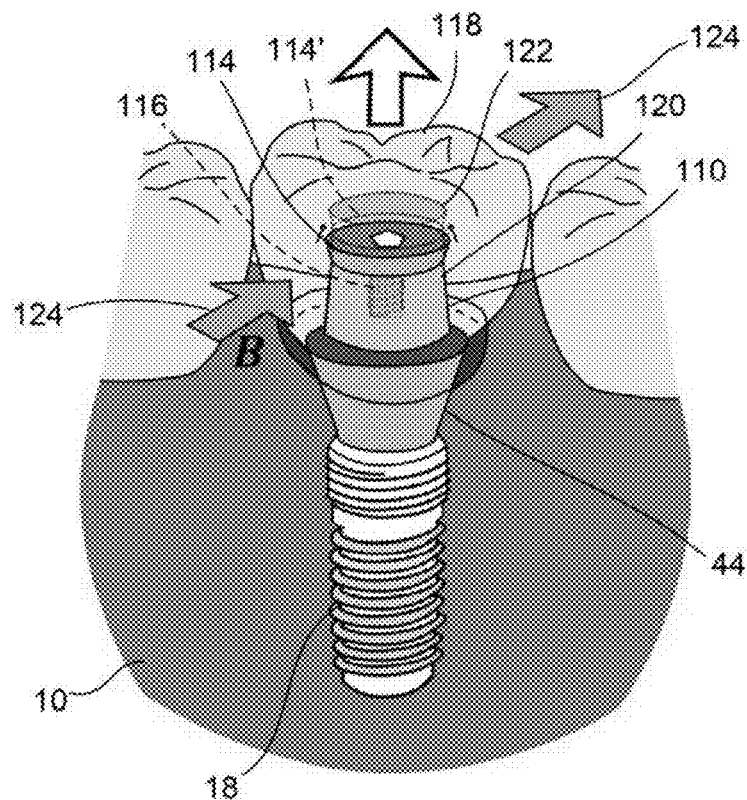
FIG. 7A illustrates the removal of the crown from the FSMA plate by application of a magnetic field to reconfigure the shape of the plate and allowing for the release of the crown.
Figure 7B:
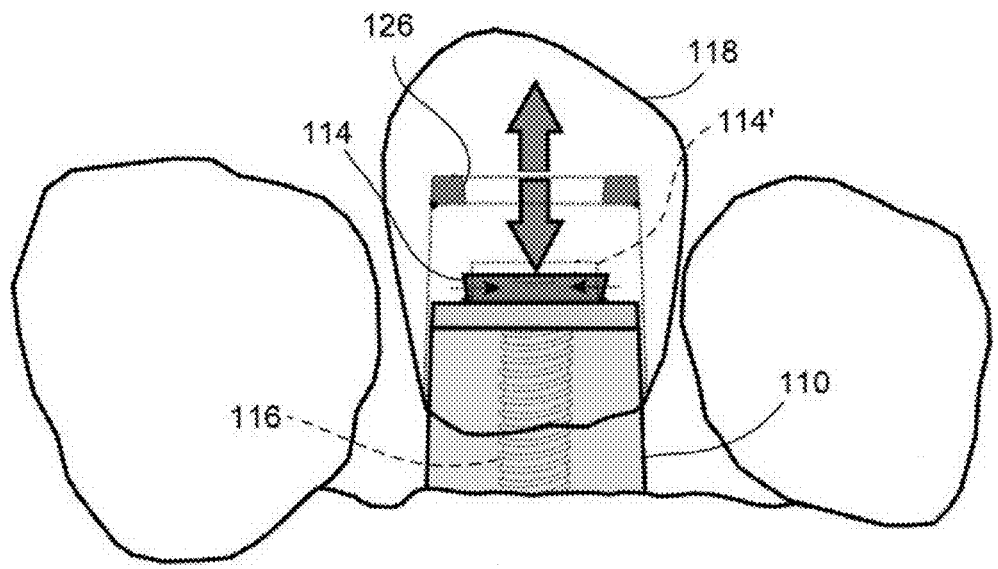
FIG. 7B illustrates a partial cross-sectional side view showing the reconfiguration of the FSMA plate and the release of the crown.

As shown in FIG. 7A, in the event that the crown 118 needs to be repositioned upon the abutment, readjusted, or removed entirely, the magnetic field 124 may be reapplied upon the crown 118 such that FSMA plate 114 reconfigures again from its tapered configuration to its straightened cylindrical configuration. FIG. 7B illustrates a partial cross-sectional side view of the FSMA plate 114 reconfigurable between its tapered configuration and its straightened configuration 114'. Also shown is another variation of the widened diameter utilizing a locking ring 126, which may be alternatively configured to define an undercut through which FSMA plate 114 may freely slide when straightened yet which interlocks against when the FSMA plate 114 is in its tapered configuration.

Figure 8:
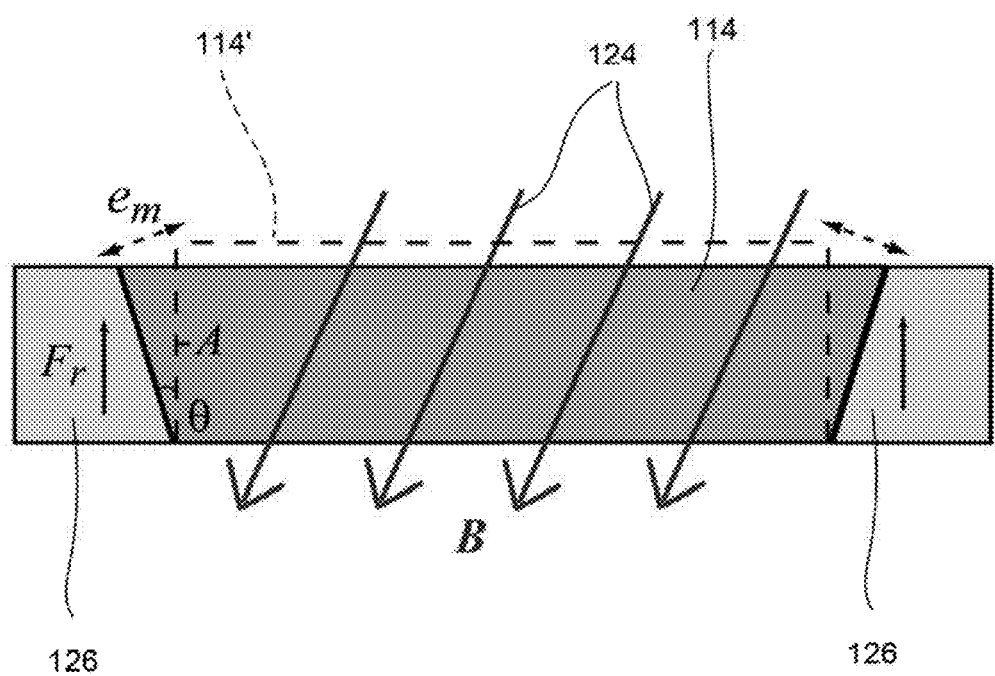
FIG. 8 illustrates a representative partial side view of an FSMA plate engaged against a widened diameter of the crown for securing the crown in position.

FIG. 8 illustrates a detail view of the locking interaction between the FSMA plate and the ring 126. With the FSMA plate 114' in its straightened configuration while under the magnetic field 124, plate 114' may freely slide into position through the ring 126. However, upon removal of the magnetic field 124, the FSMA plate 114' may reconfigure into its tapered configuration 114 such that the FSMA plate 114 is secured against the ring 126 to prevent movement of the crown relative to the plate 114. The plate 114 may be keyed relative to the ring 126 such that the crown is fitted upon the abutment in a predetermined orientation, if so desired.

In determining the amount of retention force retention force before yield $F_r$ between the plate 114 and the ring 126, the effective stress $\sigma_0$ may be initially calculated utilizing the following equation (1) while assuming that the FSMA is isotopic in nature.

$$\sigma_0 = \frac{1}{\sqrt{2}} \sqrt{\sigma_n^2 + 6\sigma_t^2} \qquad (1)$$

where $\sigma_n$ represents the normal stress and $\sigma_t$ represents the tangential stress values. Expanding the formula (1) in terms of $\sigma_0$ and $\Theta$ which represents the undercut angle, the force may be calculated utilizing the following equation (2).

$$F_R = \frac{2\sqrt{2} A}{\sqrt{(5\cos^2 2\theta + 12\cos 2\theta + 7)}} \sigma_0 \quad (2)$$

where $\sigma_n$ represents the nominal cross-sectional area of the plate 114 against the ring 126, $\Theta$ represents the undercut angle, and $\sigma_0$ represents the effective stress. Thus assuming $\cos 2\theta \approx 1$, the equation (2) for calculating the retention force may be simply reduced to the following equation (3).

$$F_R = 0.577 A \sigma_0 \quad (3)$$

Figure 9:
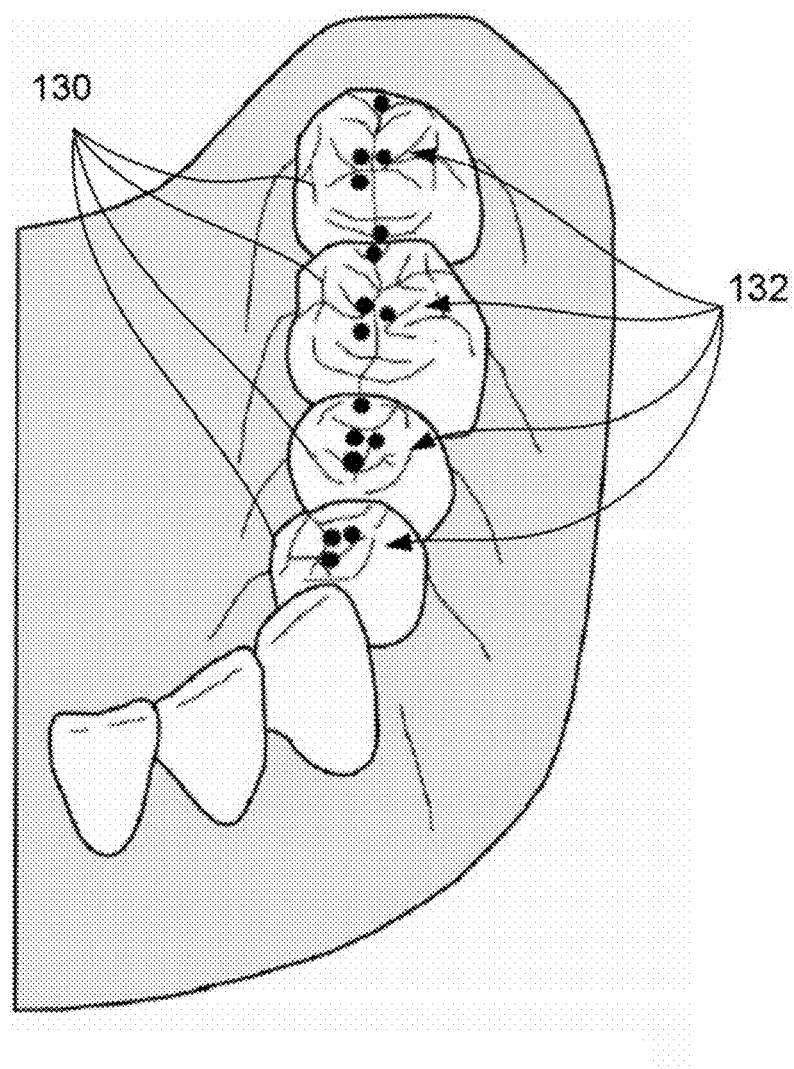
FIG. 9 shows a perspective view of one or more crowns or bridges which have been coupled to implants by utilizing the one or more elements to show how the crowns or bridges may be positioned along a patient's dentition to align the occlusal contact points for patient comfort and safety.

Because of the adjustable nature of the retention assemblies described herein, the crowns or bridges secured to the abutment assemblies may be adjusted in vivo to ensure that the dentition, once secured, aligns properly. As indicated in the perspective view of FIG. 9, multiple anchored crowns 130 as shown which have been secured to the patient. The resulting occlusal contact points 132, which are those areas along the occlusal surface which contact the opposed tooth or teeth as the jaw is articulated, may thus be adjusted utilizing the mechanisms and methods described to ensure proper alignment for patient comfort, safety, and reliability of the crowns.

Figure 10:
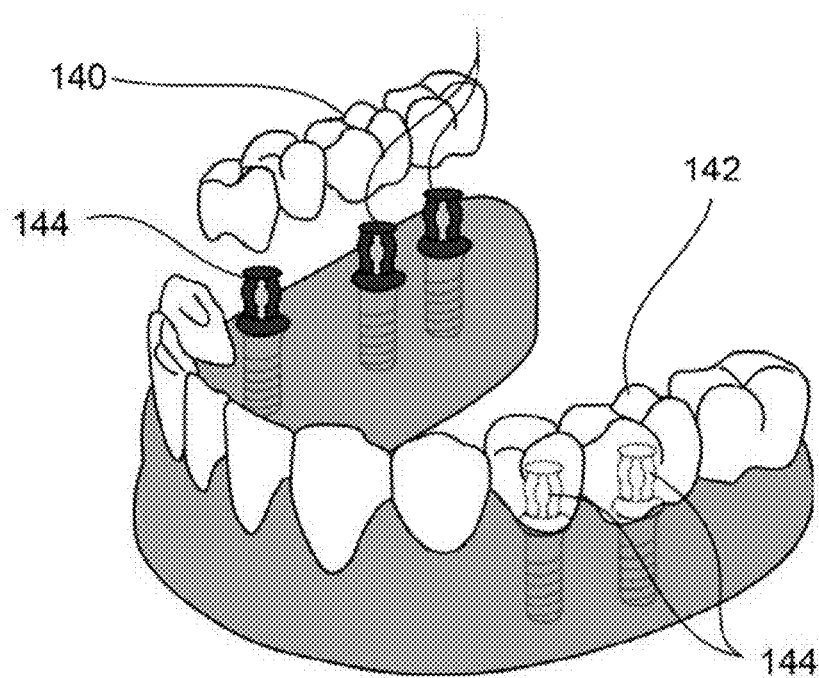
FIG. 10 shows a perspective view of multiple implants and abutment assemblies utilizing the reconfigurable plates or elements herein to secure individual crowns or bridges to a patient's bone.
Figure 11:
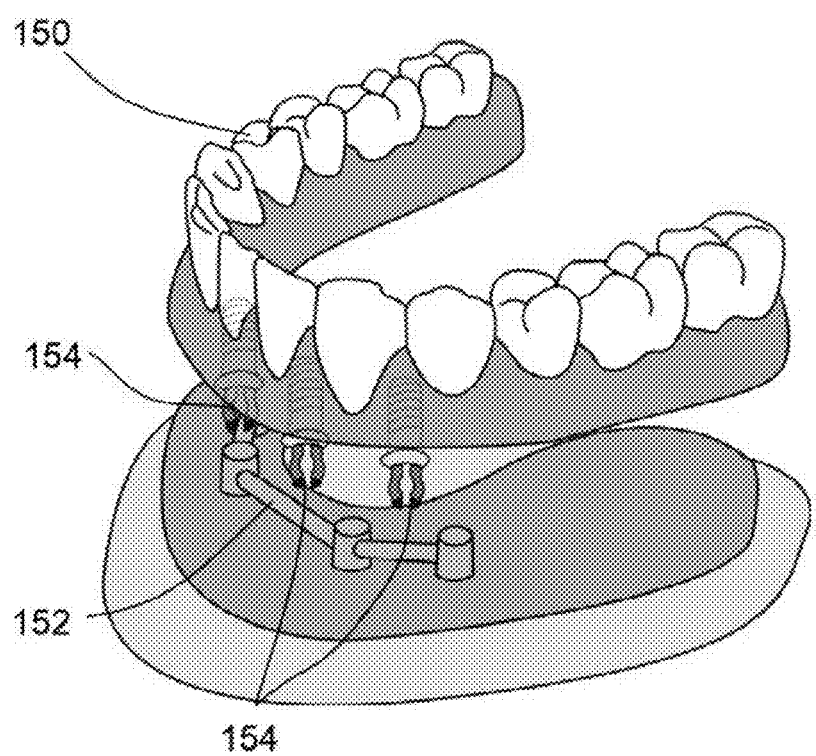
FIG. 11 shows a perspective view of another example where an implanted cross-bar may be utilized to secure an overdenture to the patient's bone via the reconfigurable plates or elements.

Although the previous examples have illustrated a single crown placed upon a single corresponding abutment assembly, alternative variations may be utilized. For instance, FIG. 10 illustrates an example where multiple implanted anchoring assemblies 144 may be secured to the patient to allow for the securement of one or more partial bridges 140, 142 utilizing the mechanisms and methods described herein. Accordingly, one or more anchoring assemblies 144 may be used to secure one or more partial bridges. In another example, FIG. 11 shows another variation where an overdenture 150 may be secured to the patient utilizing a cross-bar 152 configuration implanted into the patient's bone. The overdenture 150 itself may incorporate one or more anchoring assemblies 154 which extend away from the overdenture 150 for coupling to the cross-bar 152. The anchoring assemblies 154 may similarly utilize the one or more elements for securing the overdenture 150 within the patient mouth as they may be configured to operate in a similar manner as those previously described. For instance, rather than transitioning from an extended to a compressed configuration for compression against the interior of the dental prosthesis, anchoring assemblies 154 may transition from to an extended configuration to a compressed configuration which compresses over and/or upon the cross-bar 152 to secure the overdenture 150 thereto.

Figure 12:
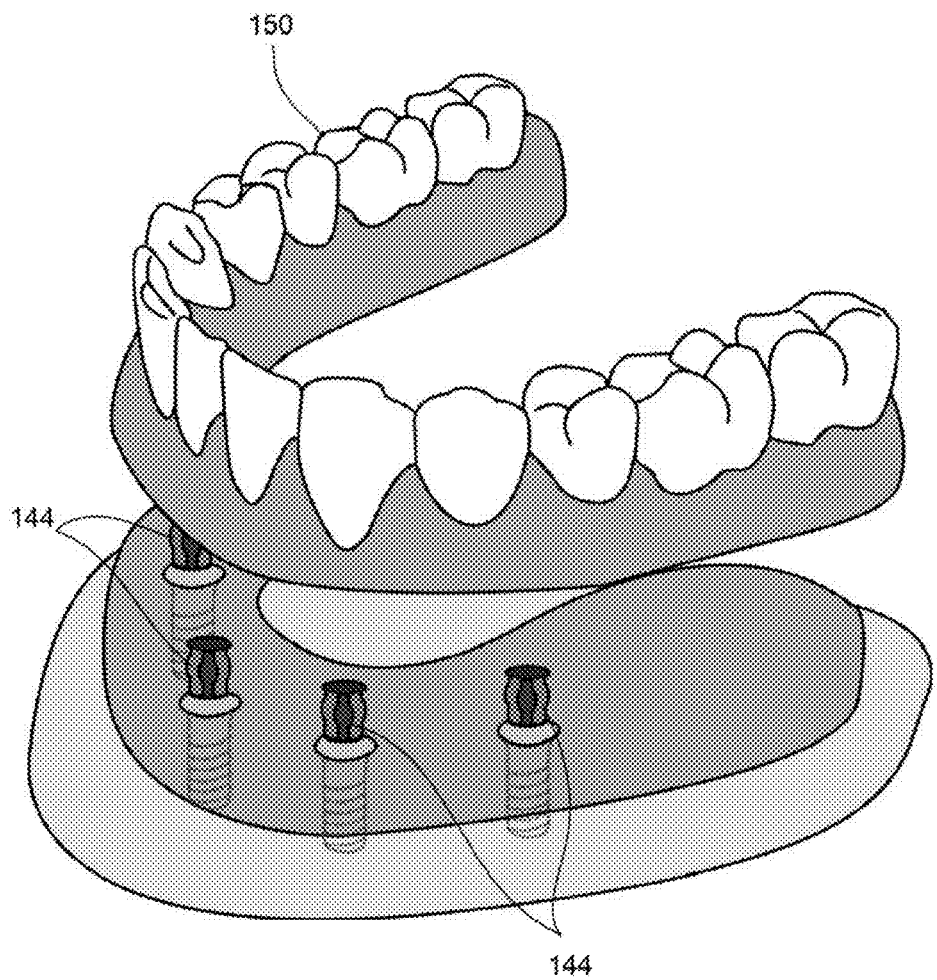
FIG. 12 shows a perspective view of yet another example where one or more anchoring assemblies may be used to secure a dental prosthesis, such as an overdenture, to the patient's mouth.

In yet another example, as shown in the perspective view of FIG. 12, one or more anchoring assemblies 144 may be secured to the patient's mouth for coupling to a dental prosthesis such as an overdenture 150. In this example, the overdenture 150 may define one or more receiving channels corresponding to the one or more anchoring assemblies 144 such that reconfiguration of the compression plates along anchoring assemblies 144 may compress and secure against an interior surface of each respective receiving channel in a manner as described above to secure the overdenture 150 within the patient's mouth. Removal of overdenture 150 may be effected utilizing any of the variations described herein to allow for daily removal of overdenture 150, if so desired.

Figure 13:
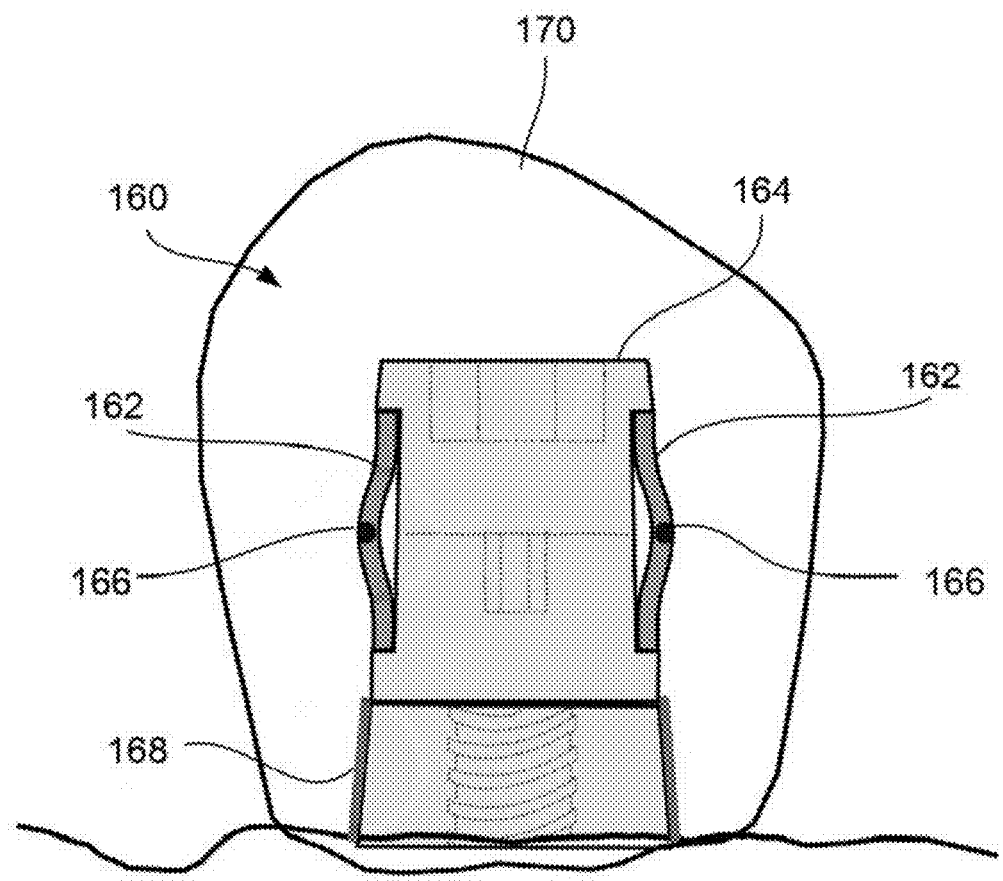
FIG. 13 shows yet another example of an anchoring assembly utilizing compression plates comprised of biased spring elements which are reconfigured by a shape memory wire.

Another variation of the anchoring assembly is illustrated in the side view of FIG. 13, which shows an anchoring assembly 160 utilizing compression plates which are comprised of biased elements 162, e.g., leaf springs, which are prefabricated to be biased in an outwardly radial direction relative to the abutment assembly 164 to which they are mounted. The biased elements 162 may be fabricated into individual plates from a material such as spring stainless steel which are formed to have a curved or arcuate portion rather than from a shape memory alloy, as previously described. Thus, when the elements 162 are positioned within or along the abutment assembly 164, the curved or arcuate portions may extend radially and function as a biased spring element.

Each of the elements 162 may define a channel or opening through which a separate shape memory wire 166, such as a wire made from a nickel-titanium alloy, may pass through. Shape memory wire 166 may be stretched relatively taut through elements 162 such that when wire 166 is energized, as previously described, the wire 166 may shorten in length to compress the curved or arcuate portions of elements 162 into a flattened configuration against abutment assembly 164 to allow for the placement or positioning of a dental prosthesis, such as a crown 170, over abutment assembly 164. Once crown 170 has been desirably positioned, energy may be removed from wire 166 to allow for its re-lengthening which in turn may allow for elements 162 to relax back into its curved or arcuate shape such that elements 162 compress against the interior surface of crown 170 thus locking or securing crown 170 into position upon the anchoring assembly 160. As previously described, a sealant 168 may also be optionally positioned upon the crown interior for forming a water-tight seal against the anchoring assembly 160 to prevent the entry of food and liquids into the crown interior.

The applications of the devices and methods discussed above are not limited to the securement of crowns or bridges but may include any number of further treatment applications where the securement and adjustability of devices within a patient may be utilized. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method of securing an oral appliance, comprising:
coupling an abutment assembly to an implant secured within a mouth of a patient, the abutment assembly having a plurality of shape memory elements secured circumferentially surrounding an upper abutment portion of the abutment assembly such that a portion of each of the shape memory elements changes its shape by extending radially relative to the abutment assembly when the shape memory elements are in a locking configuration; and
positioning a crown upon the upper abutment portion such that the portions of the shape memory elements extending radially are secured within a corresponding receiving channel defined along a coping within the crown.

2. The method of claim 1 further comprising:
actuating the one or more shape memory elements to retract into a low profile configuration such that the shape memory elements are retracted from the receiving channel; and
adjusting a position of the crown relative to the abutment assembly.

3. The method of claim 2 wherein actuating comprises applying electromagnetic energy to the one or more shape memory elements.

4. The method of claim 2 further comprising re-actuating the one or more shape memory elements to reconfigure into the locking configuration.

5. The method of claim 1 further comprising angling the abutment assembly relative to the implant.

6. The method of claim 1 further comprising inhibiting rotation of the crown relative to the abutment assembly via a non-circular cross-sectional area defined by the abutment assembly.

7. The method of claim 1, wherein the upper abutment portion extends beyond the gingiva of the patient.

8. The method of claim 1, wherein the plurality of shape memory elements radially surround the upper abutment portion.

* * * * *